United States Patent
Hua et al.

(10) Patent No.: US 9,475,789 B2
(45) Date of Patent: Oct. 25, 2016

(54) USE OF POLYENYLPYRROLE DERIVATIVES FOR TREATING INFLAMMATION

(71) Applicant: Yu-Chieh Lee, Taoyuan County (TW)

(72) Inventors: Kuo-Feng Hua, I-Lan (TW); Ann Chen, Taipei (TW); Yulin Lam, Singapore (SG); Shih-Hsiung Wu, Taipei (TW); Shuk-Man Ka, Taipei (TW); Yu-Chieh Lee, Taoyuan County (TW); Sheau-Long Lee, Taoyuan County (TW)

(73) Assignee: WELLHEAD BIOLOGICAL TECHNOLOGY CORP., Taoyuan County (TW)

( * ) Notice: Subject to any disclaimer, the term of this patent is extended or adjusted under 35 U.S.C. 154(b) by 0 days.

(21) Appl. No.: 14/243,388

(22) Filed: Apr. 2, 2014

(65) Prior Publication Data
US 2015/0284355 A1  Oct. 8, 2015

(51) Int. Cl.
*C07D 309/38*  (2006.01)
*C07D 405/06*  (2006.01)
*C07D 409/06*  (2006.01)
*A61K 31/35*  (2006.01)

(52) U.S. Cl.
CPC ............ *C07D 309/38* (2013.01); *C07D 405/06* (2013.01); *C07D 409/06* (2013.01); *A61K 31/35* (2013.01)

(58) Field of Classification Search
CPC . C07D 309/38; C07D 405/06; C07D 409/06
USPC ........................ 514/422, 444, 460
See application file for complete search history.

(56) References Cited

U.S. PATENT DOCUMENTS 7,304,034 B2 * 12/2007 Tracey et al. ...... C07K 14/4702
424/9.1

OTHER PUBLICATIONS

Fan et al. Synthesis and biological evaluation of polyenylpyrrole derivatives and anticancer agents acting through caspases-dependent apoptosis. Journal of Medicinal Chemistry 2010, 53, pp. 7967-7978.*

* cited by examiner

*Primary Examiner* — Jennifer M Kim
(74) *Attorney, Agent, or Firm* — WPAT, P.C., Intellectual Property Attorneys; Anthony King

(57) ABSTRACT

The preset invention relates to a method for treating inflammation comprising administering a subject in need thereof with a therapeutically effective amount of polyenylpyrrole derivatives of formula (I) or a pharmaceutically acceptable salt thereof.

16 Claims, 14 Drawing Sheets

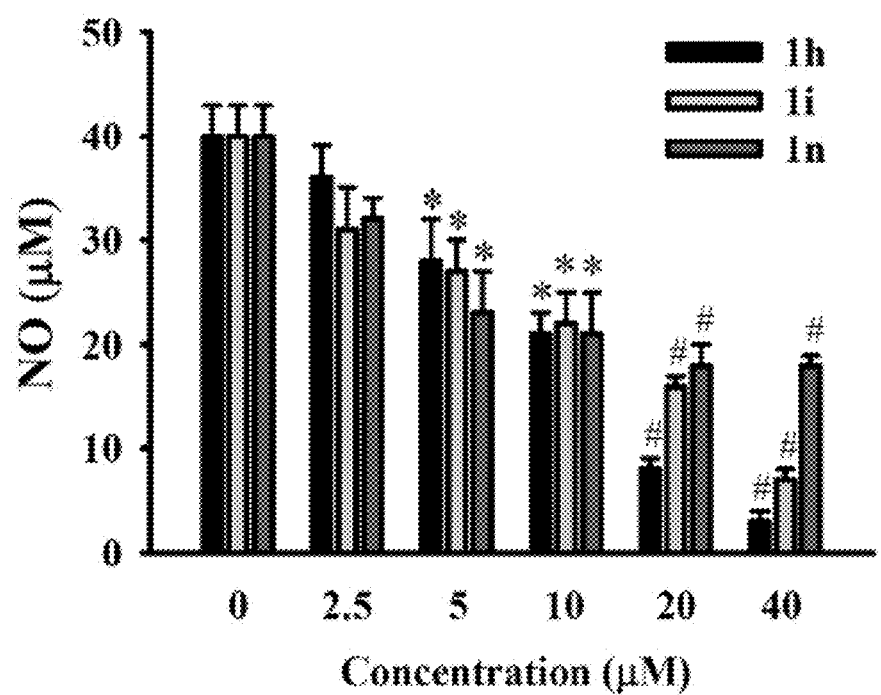
Fig.2 (cont')

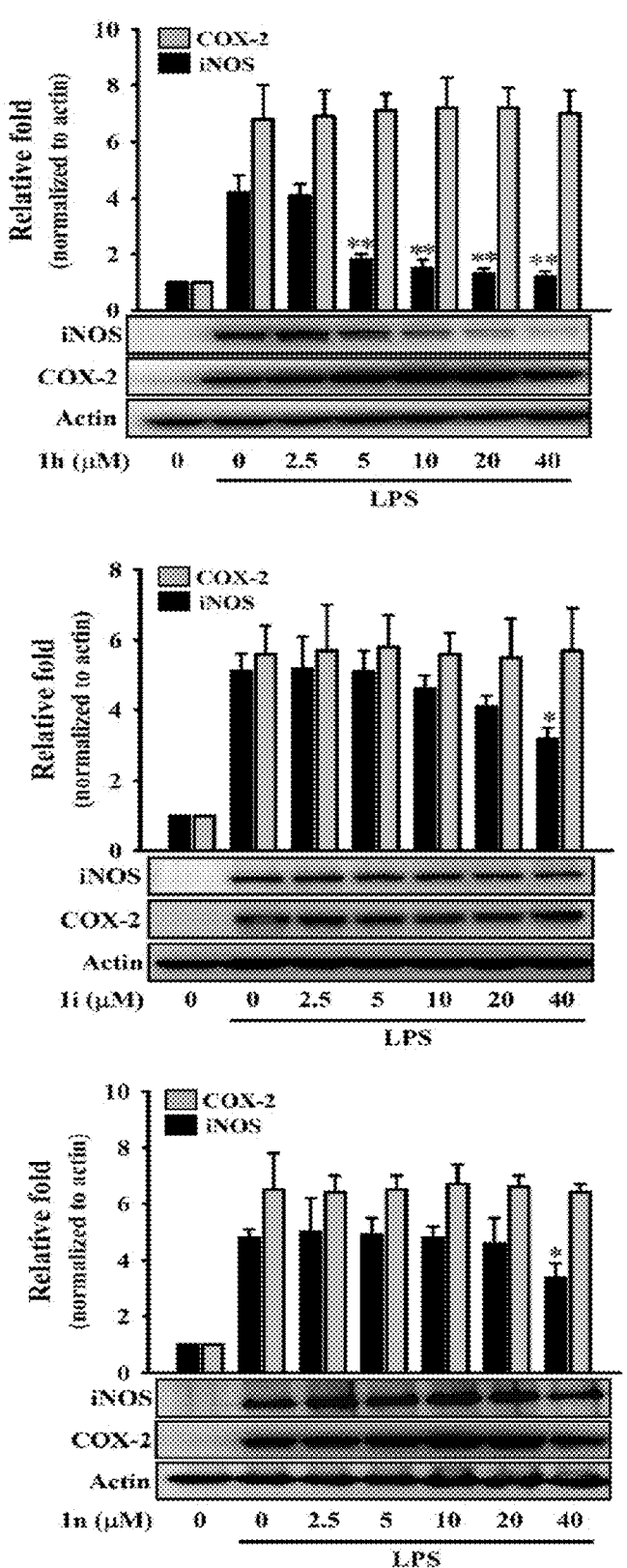
Fig.2 (cont')

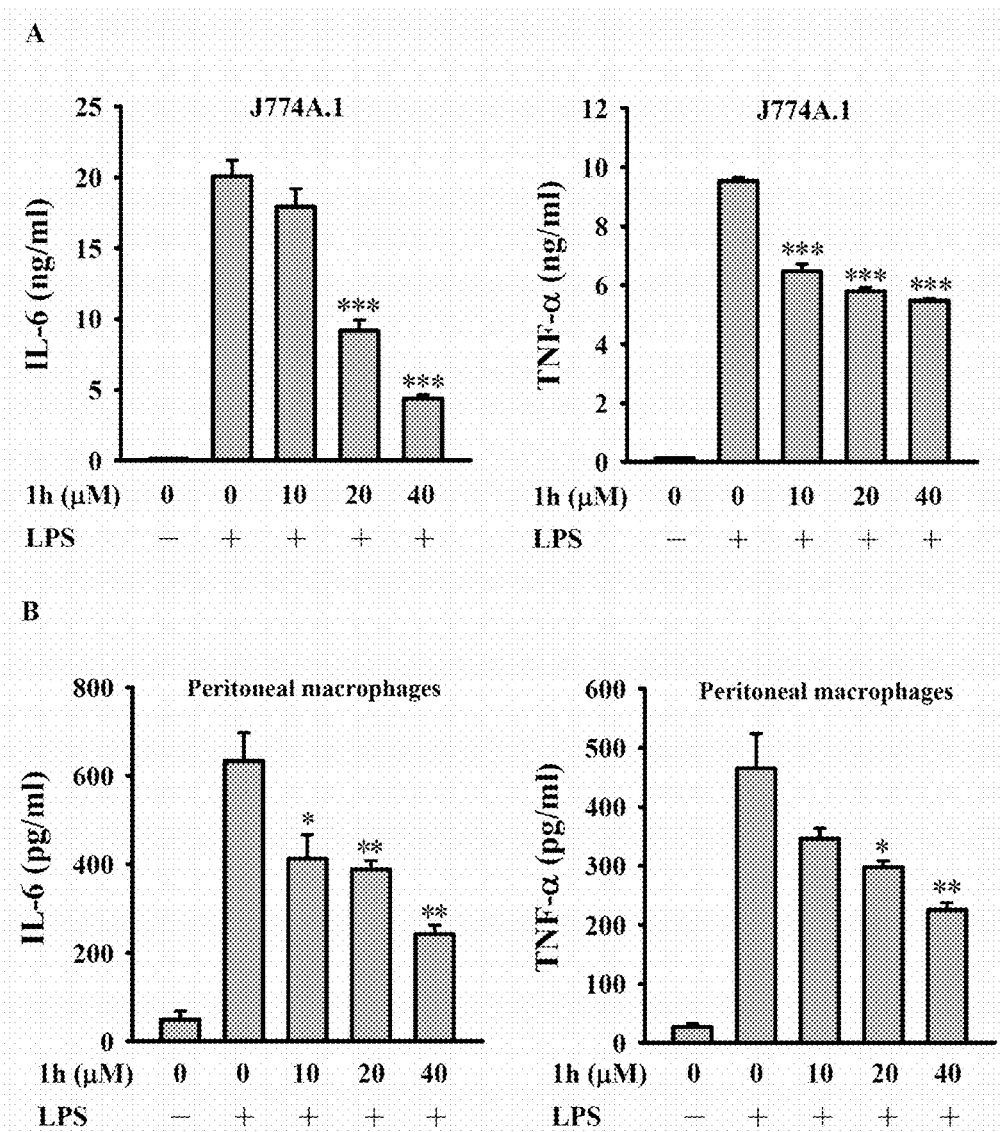
Fig. 3 (Cont')

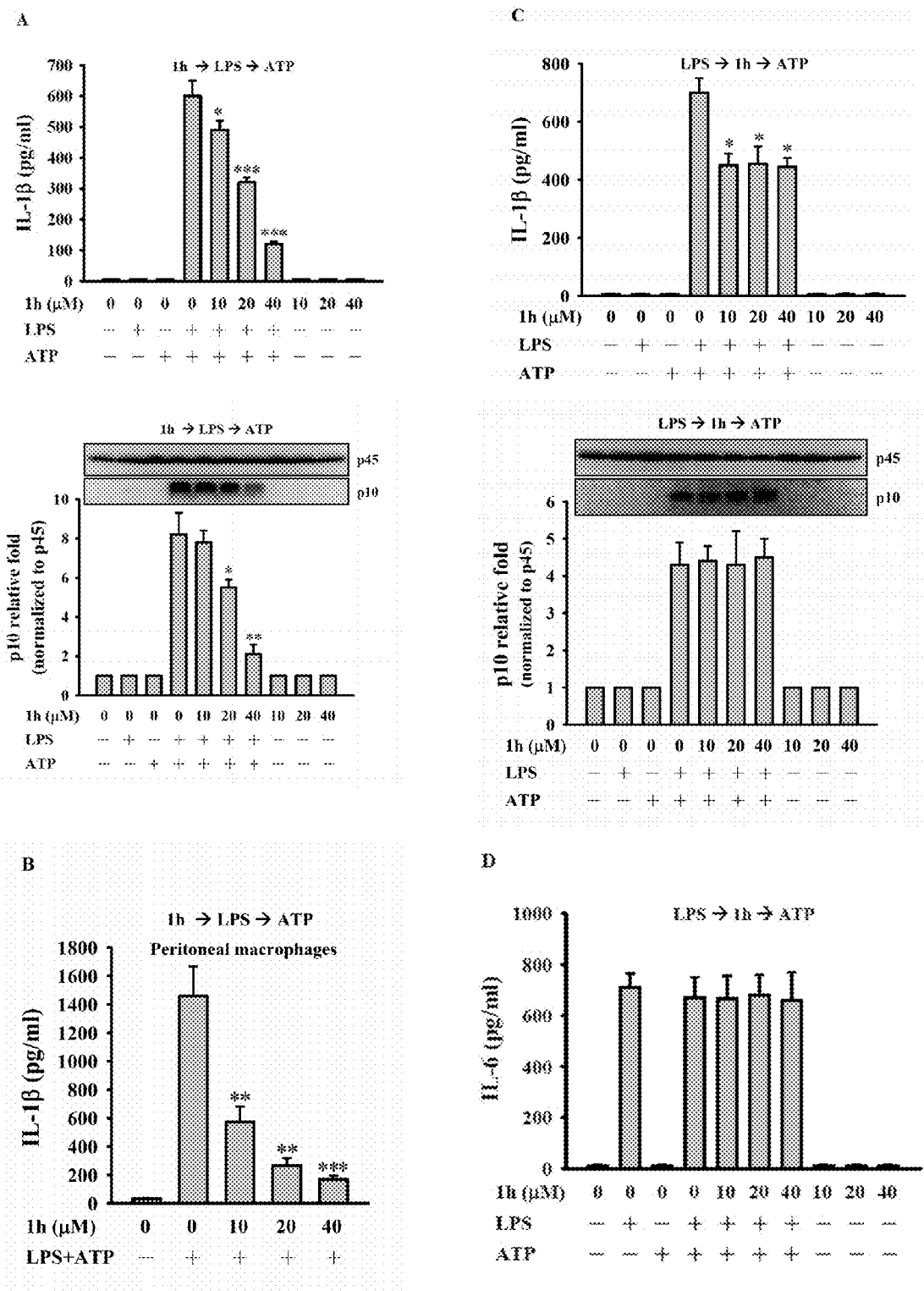
Fig. 4 (Cont')

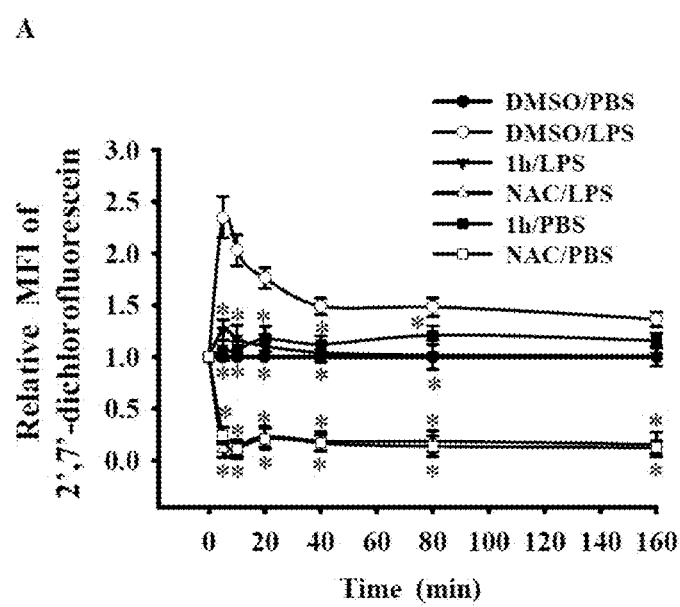
Fig. 5 (Cont')

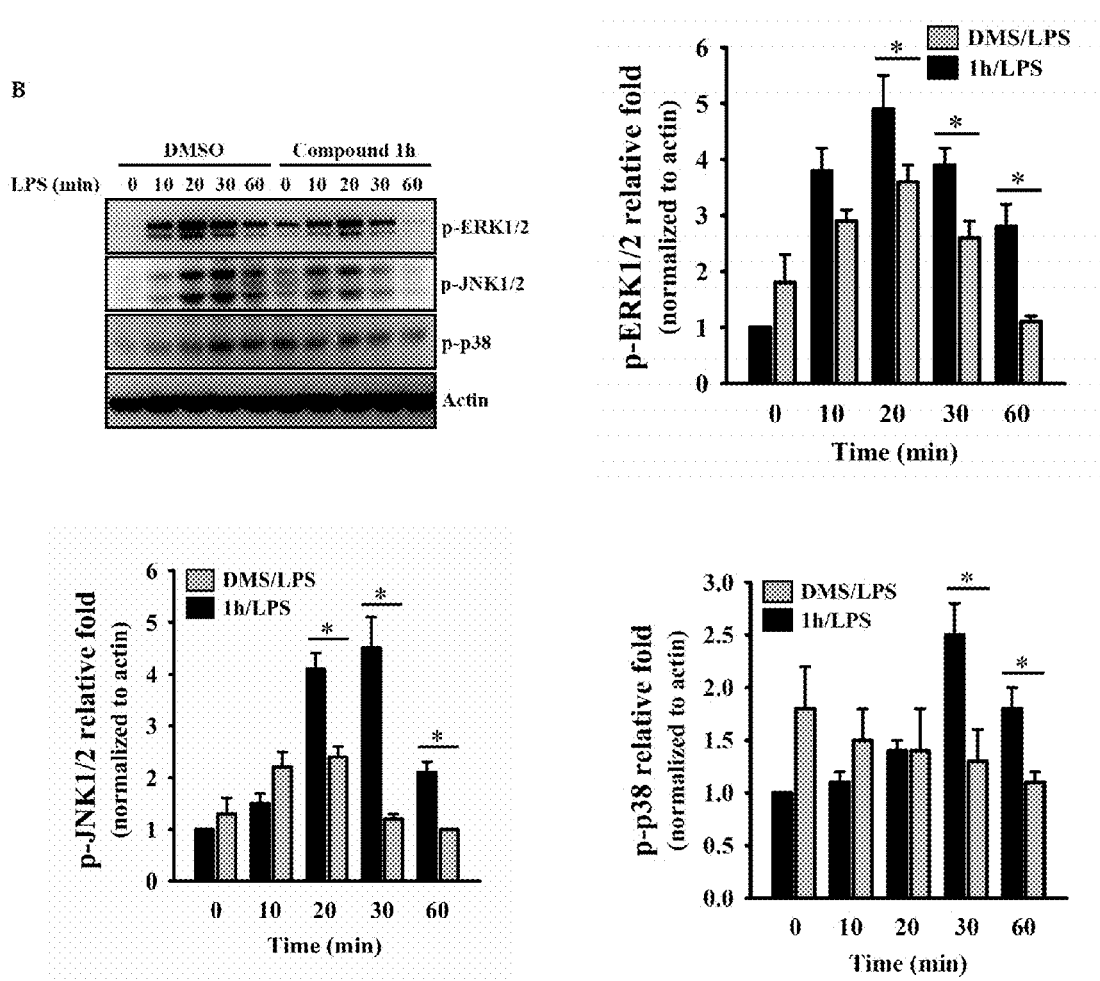
Fig. 5 (Cont')

A
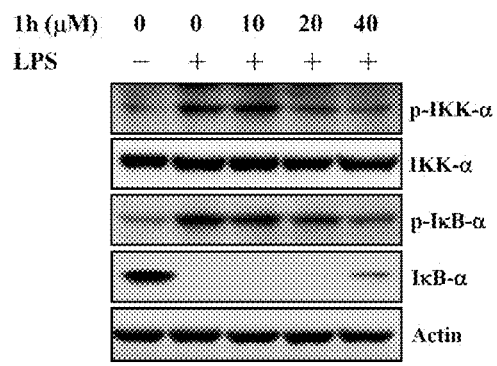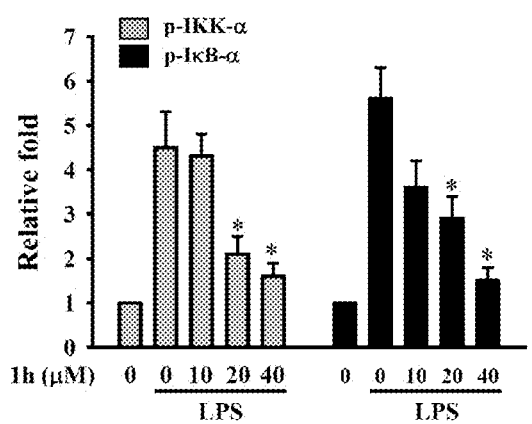
B
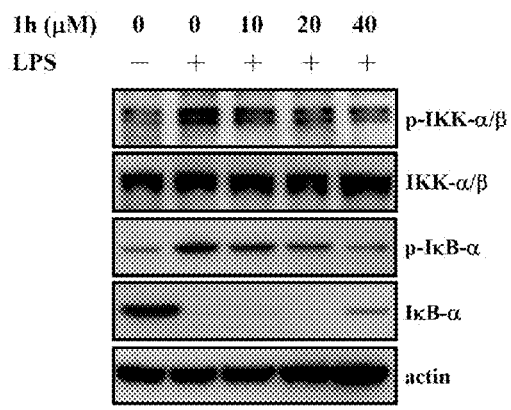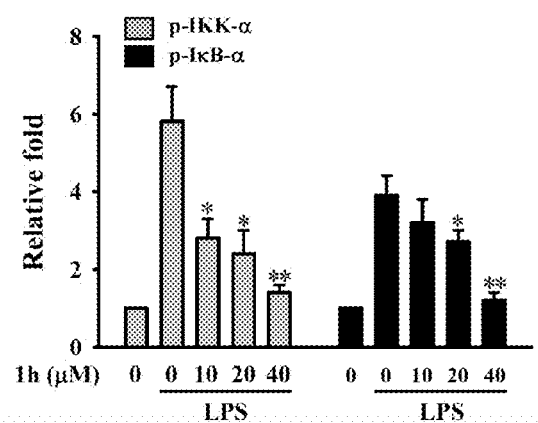
Fig. 6 (Cont')

USE OF POLYENYLPYRROLE DERIVATIVES FOR TREATING INFLAMMATION

FIELD OF THE INVENTION

The present invention relates to a new use of polyenylpyrrole derivatives for treatment of inflammation.

BACKGROUND OF THE INVENTION

Conjugated polyenes is an interesting class of widely occurring natural polyketides as they have been shown to possess excellent biological properties such as antibacterial (Shim S H et al., (2011) *J Nat Prod* 74(3): 395-401), antifungal (Shim S H et al. supra; Chomcheon P et al., (2010) *Chemistry* 16(36): 11178-11185) and antitumor activities (Gross H et al. (2009) *Org Lett* 11(21): 5014-5017; Yang Y L et al. (2007) *Chemistry* 13(24): 6985-6991).

Inflammation occurs in response to numerous conditions including physical injury, irritation, tumor growth in tissue, and bacterial, parasitic, fungal, or viral infection. Inflammation causes both local and systemic effects. Representative effects that can occur at the site of injury, irritation, or disease are the increase of vascular permeability, release of degradative enzymes including metalloproteinase, migration of leukocytes to the affected site, neutrophil burst response to destroy invading cells, and the secretion of cytokines Important systemic effects include pain, fever, and the acute response in the liver.

Inflammatory cells include lymphocytes, mononuclear macrophages and dendritic cells. Once activated, these inflammatory cells can induce a series of inflammatory responses by releasing inflammatory mediators, against the infections or foreign particles. Further, nitric oxide (NO), interleukin-6 (IL-6), and TNF-α are important pro-inflammatory mediators that are produced mainly by lipopolysaccharide (LPS)-activated macrophages and mediate multiple biological effects, including the activation of immune responses. Additionally, the inflammasome is a multi-protein signal complex for activating caspase-1. Among the inflammasome, the NLRP3 inflammasome is one of the most well-studied. The NLRP3 inflammasome is activated by adenosine triphosphate in LPS-activated macrophages, leading to caspase-1 activation and IL-1β secretion (Hu Y, et al., *J Immunol.* 2010 Dec. 15; 185(12):7699-705).

In our previous works, we isolated certain polyketides from thermophilic fungus *Myceliophthora thermophila*, and demonstrated that some of these compounds exhibited anti-tumor activity (Yang Y L et al. supra). We also synthesized a class of polyenylpyrroles and their analogs which were evaluated for their anti-tumor activities. However, the anti-inflammation activities of the polyenylpyrrole derivatives are not disclosed.

BRIEF SUMMARY OF THE INVENTION

In this present invention, it is unexpectedly found that polyenylpyrrole derivatives of formula (I) as defined herein exhibit excellent anti-inflammatory activities. Particularly, these compounds are non-cytotoxic to cells. Therefore, the present invention provides a new approach for treatment of inflammation with these polyenylpyrrole derivatives.

In one aspect, the invention provides a method for treatment of inflammation comprising administering a subject in need thereof with a therapeutically effective amount of a compound of formula (I) or a pharmaceutically acceptable salt thereof:

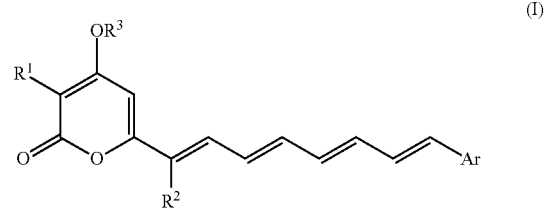

(I)

wherein $R^1$, $R^2$ and $R^3$ independently are H or an alkyl, and Ar is an aryl group or a five-membered heteroaryl group containing one, two or three heteroatoms selected from the group consisting of N, O and S, wherein the aryl group and the heteroaryl group are unsubstituted or substituted by one or two substituents independently selected from the group consisting of halo and mesyl, provided that when $R^3$ is a methyl group, Ar is not a 3-chloropyrrolyl group.

Also provided is use of the compound of formula (I) as described herein in the manufacture of a medicament for treatment of inflammation.

In certain embodiments of the invention, the aryl group is a 6-membered monocyclic, 10-membered bicyclic, or 14-membered tricyclic aryl group. Examples of an aryl group include without limitation phenyl, naphthyl, pyrenyl, anthryl, and phenanthryl.

In certain embodiments of the invention, the five-membered heteroaryl group is selected from the group consisting of pyrrolyl, furanyl, thiophenyl, oxazolyl, isoxazolyl, pyrazolyl, thiazolyl, isothiazolyl, triazolyl, oxadiazolyl, and thiadiazolyl.

In one embodiment of the invention, $R^1$ is H or methyl.
In one embodiment of the invention, $R^3$ is H or methyl.
In one embodiment of the invention, $R^2$ is H.

In some embodiments of the invention, Ar is selected from the group consisting of 3-chloropyrrol-2-yl, 3-chlorothiophen-2-yl, 2-chlorophenyl, and 3-chloro-1-mesyl-pyrrol-2-yl.

In certain examples of the invention, the compound of formula (I) is selected from the group consisting of compound 1h, compound 1i, compound 1j, compound 1k, compound 1l, compound 1m and 1n, having the structures as follows

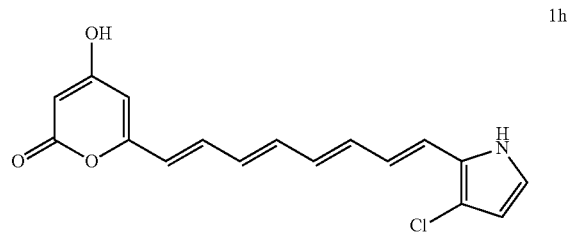

1h

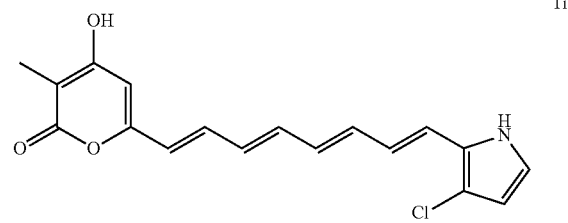

1i

-continued

1j: [structure: OMe-substituted pyranone linked via tetraene to 3-chlorothiophene]

1k: [structure: OMe and methyl-substituted pyranone linked via tetraene to 3-chlorothiophene]

1l: [structure: OMe and methyl-substituted pyranone linked via tetraene to 2-chlorophenyl]

1m: [structure: OMe and methyl-substituted pyranone linked via tetraene to 3-chlorophenyl]

1n: [structure: OMe and methyl-substituted pyranone linked via tetraene to N-sulfonyl-3-chloropyrrole]

In an embodiment of the invention, the compound of formula (I) is in a therapeutically effective amount to (i) inhibit NO production or iNOS, IL-6 or TNF-α expression, (ii) inhibit NLRP3 inflammasome-mediated IL-1β expression, or (iii) inhibit reactive oxygen species (ROS) production, mitogen-activated protein kinase (MAPR) phosphorylation, NF-κB activation or protein kinase C (PKC) activation, in inflammatory cells of the subject.

In an embodiment of the invention, the inflammatory cells are macrophages or dendritic cells.

Also provided is a composition for use in treating inflammation comprising the compound of formula (I) as described herein. Further provided is use of a compound of formula (I) as described herein for manufacture of a medicament for treating inflammation. The details of one or more embodiments of the invention are set forth in the description below.

Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments. It should be understood, however, that the invention is not limited to the preferred embodiments shown. In the drawings.

DETAILED DESCRIPTION OF THE INVENTION

Figure 1:
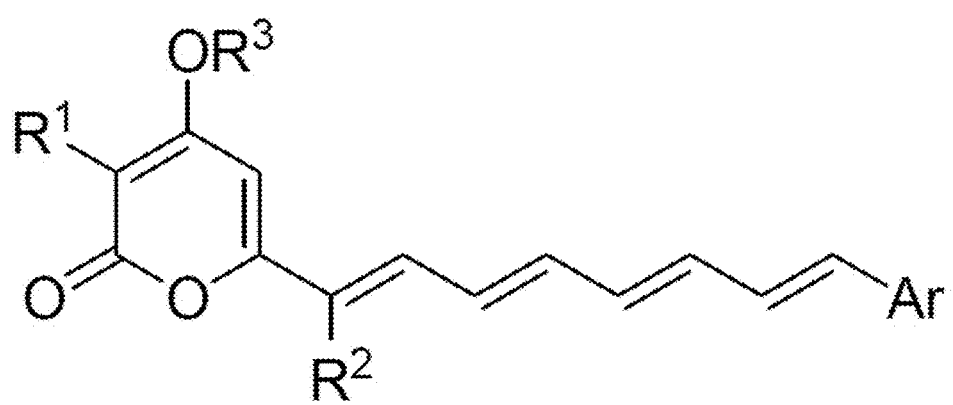
FIG. 1 shows the backbone of the synthesized polyenylpyrroles.

The following description is merely intended to illustrate various embodiments of the invention. As such, specific embodiments or modifications discussed herein are not to be construed as limitations to the scope of the invention. It will be apparent to one skilled in the art that various changes or equivalents may be made without departing from the scope of the invention.

In order to provide a clear and ready understanding of the present invention, certain terms are first defined. Additional definitions are set forth throughout the detailed description. Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The table below shows the abbreviations for some terminologies.

| | |
|---|---|
| NO | nitric oxide |
| IL-6 | interleukin-6 |
| TNF-α | tumor necrosis factor-α |
| IL-1β | interleukin-1β |
| LPS | lipopolysaccharide |
| ATP | adenosine triphosphate |
| TLR | toll-like receptor |
| COX-2 | cyclooxygenase-2 |
| ROS | reactive oxygen species |
| MAPK | mitogen-activated protein kinase |
| PKC | protein kinase C |

Innate immunity is typically triggered by pathogen-associated molecular patterns that are shared by groups of different microbial pathogens which are recognized by toll-like receptor (TLR) or other cellular receptor expressed on the cell surface of immune cells (Medzhitov R, Janeway C A. (1997) *Cell* 91: 295-298). LPS is one kind of pathogen-associated molecular patterns of gram-negative bacteria which is able to induce inflammatory mediator expression including NO, TNF-α, and IL-6 by binding to TLR4 (Takeda K, Kaisho T, Akira S. (2003) *Annu. Rev. Immunol* 21: 335-376). Unlike other cytokines, IL-1β is synthesized as an inactive immature form (precursor of IL-1β, proIL-1β) via transcriptional activation in activated macrophages (Hsu H Y, Wen M H. (2002) *J Biol Chem* 277(25): 22131-22139). IL-1β release is controlled by NLRP3 inflammasome, a multi-proteins complex containing caspase-1 (Cassel S L, Joly S, Sutterwala F S. (2009) *Semin Immunol* 21(4): 194-198; Jin C, Flavell R A. (2010) *J Clin Immunol* 30(5): 628-631). NLRP3 inflammasome controls the disease progression and inflammatory responses caused by infection (Kanneganti T D et al. (2006) *Nature* 440(7081): 233-236; Allen I C et al. (2009) *Immunity* 30(4): 556-565; Gross O et al. (2009) *Nature* 459(7245): 433-436), obesity (Vandanmagsar B et al. (2011) *Nat Med* 17(2): 179-188), cholesterol crystals, (Duewell P et al. (2010) *Nature* 464(7293): 1357-1361), silica crystals (Hornung V et al. (2008) *Nat Immunol* 9(8): 847-856), amyloid-beta (Halle A et al. (2008) *Nat Immunol* 9(8): 857-865), and uric acid crystals etc. (Martinon F et al. (2006) *Nature* 440(7081): 237-241). Recent findings suggest that ROS regulates either NLRP3 inflammasome activation or TLR4 signaling (Hsu H Y et al. (2010) *Eur J Immunol* 40(3): 616-619; Liao P C et al. (2010) *J Agric Food Chem* 58(19): 10445-10451) and inhibition of NLRP3 activation is one of the therapeutic strategies for inflammatory related diseases (Tsai P Y et al. (2011) *Free Radic Biol Med* 51(3): 744-754).

In this invention, it is unexpectedly found that the polyenylpyrrole derivatives of formula (I) have anti-inflammatory activities, particularly in terms of the effects in reducing NO expression, and also reducing expression of iNOS, IL-6 or TFN-α, and inhibiting NLRP3 inflammasome-mediated IL-1β expression, but do not decrease the expression of COX-2. It is also found that the underlying mechanisms for the anti-inflammatory activities of the polyenylpyrrole derivatives of formula (I) of the invention involves the decreasing ROS production, MAPK phosphorylation, and NF-κB activation, as well as ATP-induced ROS production and PKC-α phosphorylation.

Therefore, the invention provides a method for treatment of inflammation comprising administering a subject in need thereof a therapeutically effective amount of a compound of formula (I) or a pharmaceutically acceptable salt thereof:

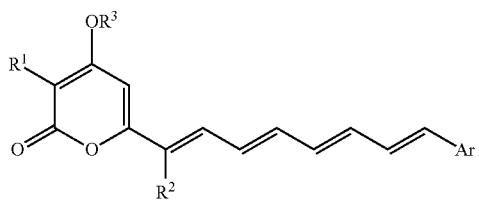

wherein $R^1$, $R^2$ and $R^3$ independently are H or an alkyl, and Ar is an aryl group or a five-membered heteroaryl group containing one, two or three heteroatoms selected from the group consisting of N, O and S, wherein the aryl group and the heteroaryl group are unsubstituted or substituted by one or two substituents independently selected from the group consisting of halo and mesyl, provided that when $R^3$ is a methyl group, Ar is not a 3-chloropyrrolyl group.

Also provided is a composition for use in treating inflammation comprising the compound of formula (I) as described herein. Further provided is use of a compound of formula (I) as described herein for manufacture of a medicament for treating inflammation.

As used herein, the term "alkyl" refers to a straight or branched monovalent hydrocarbon containing, unless otherwise stated, 1-20 carbon atoms (e.g., $C_1$-$C_{10}$, $C_1$-$C_8$, or $C_1$-$C_4$,). Examples of alkyl include, but are not limited to, methyl, ethyl, n-propyl, i-propyl, n-butyl, i-butyl, and t-butyl.

As used herein, the term "aryl" refers to a monovalent 6-carbon monocyclic, 10-carbon bicyclic, 14-carbon tricyclic aromatic ring system. Examples of aryl groups includes without limitation phenyl, naphthyl, pyrenyl, anthryl, and phenanthryl. In one example, the aryl group is phenyl. The term "heteroaryl" as used herein refers to a five membered monocyclic aromatic ring system having one, two or three heteroatoms such as N, O and/or S. Examples of heteroaryl groups includes without limitation pyrrolyl, furanyl, thiophenyl, oxazolyl, isoxazolyl, pyrazolyl, thiazolyl, isothiazolyl, triazolyl, oxadiazolyl, and thiadiazolyl. Preferred examples of heteroaryl groups are pyrrolyl and thiophenyl. The aryl and heteroaryl groups are unsubstituted or substituted by one or two substituents, including without limitation, halo or mesyl ($CH_3SO_2$—).

In some embodiments of the invention, $R^1$ and $R^3$ are independently H or methyl, and $R^2$ is H.

In some embodiments of the invention, Ar is selected from the group consisting of 3-chloropyrrol-2-yl, 3-chlorothiophen-2-yl, 2-chlorophenyl, and 3-chloro-1-mesyl-pyrrol-2-yl.

Specifically, Table 1 shows exemplary compounds of formula I of the invention.

TABLE 1

| Example | $R^1$ | $R^2$ | $R^3$ | Ar |
|---|---|---|---|---|
| 1h | H | H | H | 3-chloropyrrol-2-yl |
| 1i | Me | H | H | 3-chloropyrrol-2-yl |
| 1j | H | H | Me | 3-chlorothiophen-2-yl |
| 1k | Me | H | Me | 3-chlorothiophen-2-yl |
| 1l | Me | H | Me | 2-chlorophenyl |
| 1m | Me | H | Me | 3-chlorophenyl |
| 1n | Me | H | Me | 3-chloro-1-mesyl-pyrrol-2-yl |

The structures of the exemplified compounds are as follows:

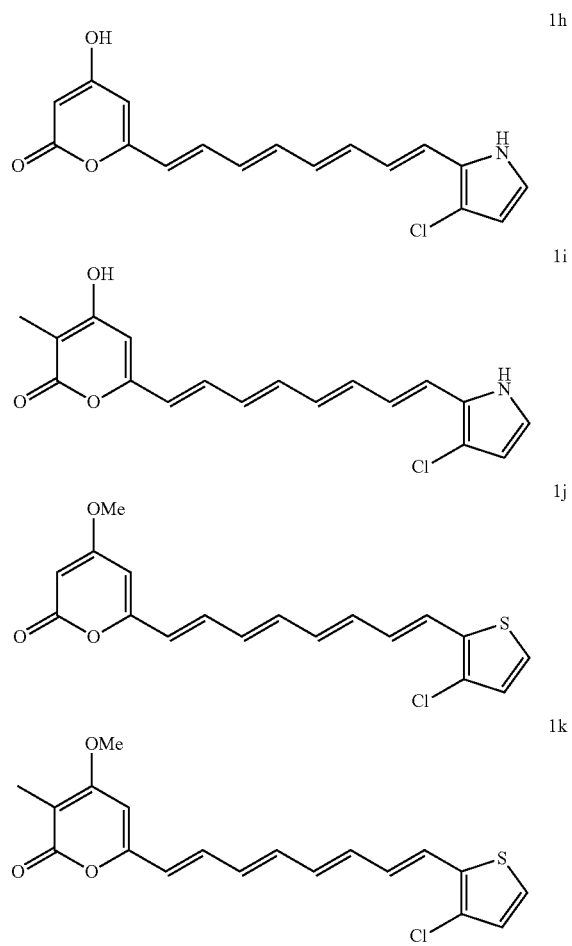

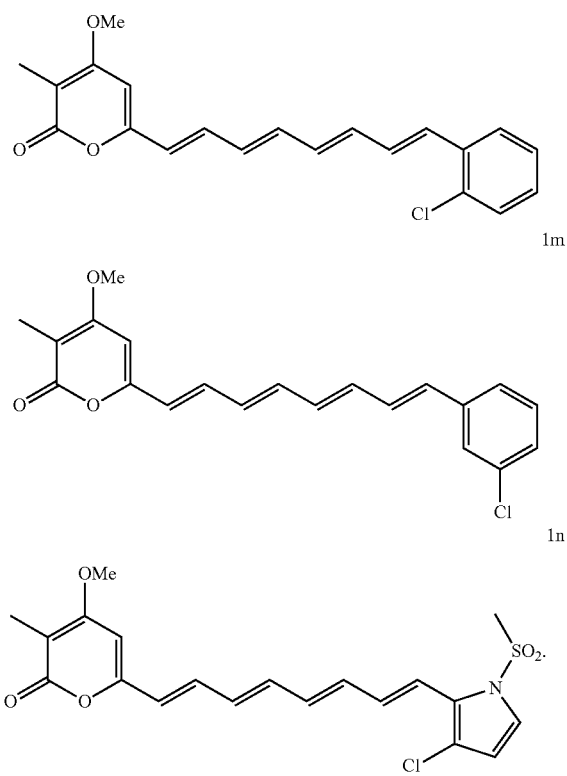

As used herein, the term "treating" as used herein refers to application or administration of one or more active agents to a subject, who has a disease, a symptom of the disease or a predisposition toward the disease, with the purpose to cure, heal, alleviate, relieve, alter, remedy, ameliorate, improve, or affect the disease, the symptom of the disease, or the predisposition toward the disease. For example, the term "treating inflammation or an inflammatory disorder" as used herein will refer to reducing local or systemic inflammatory over-responses by inhibiting NO, iNOS, IL-6 or TNF-α expression and inhibiting NLRP3 inflammasome-mediated IL-1β expression, but does not decrease the expression of COX-2.

The term "effective amount" as used herein refers to that amount of an active agent or composition sufficient to achieve the above-described therapeutic efficacies in a subject. The effective amount may vary, for example, depending upon the types or dosage of the agent or composition and the weight, age and healthy condition of the subject to be treated.

As used herein, the term "subject" as used herein includes human beings and animals, such as companion animals (e.g., dogs, cats, and the like), farm animals (e.g., cows, sheep, pigs, horses, and the like), or laboratory animals (e.g., rats, mice, guinea pigs, and the like).

As used herein, the term "inflammatory disorder" as used herein includes rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, juvenile dermatomyositis, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

The term "pharmaceutically acceptable salt" as used herein refers to a salt which is not deleterious to the subject to be treated and retain the biological effectiveness and properties of the active compound. Salts may also be derived from the following pharmacologically or physiologically acceptable inorganic and organic acids: hydrochloric, hydrobromic, sulfuric, nitric, fumaric, phosphoric, diphosphate, succinic, tartaric, acetic, citric, methanesulfonic, formic, benzoic, and malonic, but not being limited therein. Salts may also be derived from the following pharmacologically or physiologically acceptable inorganic and organic bases: alkali metal (e.g. sodium), alkaline earth metal (e.g. magnesium), and ammonium salts, but not being limited therein.

The compounds of the invention may be administered by a medically acceptable route such as orally, parentally (e.g. intramuscularly, intravenously, subcutaneously, interperitoneally), transdermally, rectally, by inhalation and the like.

In addition, the compounds of the invention are preferably formulated with a pharmaceutically acceptable carrier to form a pharmaceutical composition for use in the above mentioned treatments. Accordingly, the present invention further relates to a pharmaceutical composition comprising at least one of the compounds as described above or a pharmaceutically acceptable salt thereof together with a pharmaceutically acceptable carrier, for use in the treatment as described herein.

The carrier may serve as a diluent, vehicle, excipient, or medium for the active ingredient. Some examples of suitable excipients include saline, buffered saline, dextrose, water, glycerol, ethanol, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, syrup, and methyl cellulose. The composition can additionally include lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be in any forms as desired, including but not limited to, tablets, pills, powders, lozenges, sachets, cachets, suppositories, suspensions, emulsions, solutions, syrups, soft and hard gelatin capsules, sterile injectable solutions, packaged powders, mist, implants or patches. The compositions of the invention may be prepared by conventional methods known in the art of pharmacy.

Without further elaboration, it is believed the above description has adequately enabled the present invention.

The following example is, therefore, to be construed as merely illustrative, and does not limit of the remainder of the disclosure in any way whatsoever. All of the publications, including patents, cited herein are hereby incorporated by reference in their entireties.

The present invention is further illustrated by the following examples, which are provided for the purpose of demonstration rather than limitation.

EXAMPLE

1. Materials and Methods

1.1 Materials

Based on the chemical structure of polyenylpyrroles, auxarconjugatin A and 12E-isorumbrin, we synthesized a class of polyenylpyrroles and their analogues. The 3-chloropyrrole group plays an important role in the cytotoxicity effects of auxarconjugatin A and 12E-isorumbrin; therefore, the 3-chloropyrrole is replaced with other 2- or 3-chloro-substituted aromatic rings. The different R positions of polyenylpyrroles are replaced with H, Me, or n-Bu. The backbone of the synthesized polyenylpyrroles was shown in FIG. 1 (Fang Z et al. (2010) *J Med Chem* 53(22): 7967-7978).

LPS (from *Escherichia coli* 0111:B4), ATP, mouse antibodies against mouse phospho-ERK1/2, phospho-JNK1/2, phospho-p38, and actin were purchased from Sigma (St. Louis, Mo.). Rabbit antibodies against mouse phospho-IKK-α/β, IKK, phospho-IκB-α, IκB-α, phospho-PKC-α, IL-1β, caspase-1, iNOS, and COX-2, rabbit antibodies against mouse phospho-IKK-α/β, and horseradish peroxidase-labeled second antibodies were obtained from Santa Cruz Biotechnology (Santa Cruz, Calif. ). NLRP3 antibody was purchased from Enzo Life Sciences, Inc. (Farmingdale, N.Y.). IL-1β, TNF-α and IL-6 ELISA kits were purchased from R&D Systems (Minneapolis, Minn.).

1.2 Cell Cultures

Murine macrophages RAW 264.7 and J774A.1 cells, and immortalized C57BL/6 murine bone marrow-derived dendritic cell line JAWSII, were purchased from American Type Culture Collection (CRL-11904). RAW 264.7 macrophages stably transfected with the NF-κB reporter gene (RAW-Blue™ cells) were purchased from InvivoGen (San Diego, Calif.). RAW 264.7, J774A.1, and RAW-Blue™ cells were grown in RPMI-1640 medium supplemented with 10% heat-inactivated fetal bovine serum (FBS) (Life Technologies, Carlsbad, Calif.). JAWSII cells were grown in RPMI-1640 medium supplemented with 20% non-inactivated FBS and 5 ng/ml murine GM-CSF (R&D Systems). All cells were cultured at 37° C. in a 5% $CO_2$ incubator.

1.3 AlamarBlue® Assay for Cell Viability

RAW 264.7 cells were seeded at a density of 5000 cells in 100 µl RPMI 1640 medium with 10% heat-inactivated FBS per well in 96-well flat-bottom plates and incubated for 24 h at 37° C. in a 5% $CO_2$ incubator. Cells were incubated with tested samples for 24 h and the AlamarBlue® assay was used to determine the cytotoxicity of the test samples. The procedure was conducted following the protocol described in the manufacture's instruction (AbD Serotec Ltd).

1.4 Enzyme-Linked Immunosorbent Assay (ELISA)

The effects of tested samples on IL-1β, TNF-α and IL-6 production were measured by ELISA according to the manufacturer's instruction. In brief, 50 µl of biotinylated antibody reagent and 50 µl of supernatant were added to an anti-mouse IL-1β, TNF-α and IL-6 precoated stripwell plate, and incubated at room temperature for 2 h. After washing the plate three times with washing buffer, 100 µl of diluted streptavidin-HRP concentrate was added to each well and incubated at room temperature for 30 min. The washing process was repeated; then 100 µl of a premixed tetramethylbenzidine substrate solution was added to each well and developed at room temperature in the dark for 30 min. Following the addition of 100 µl of stop solution to each well to stop the reaction, the absorbance of the plate was measured by a microplate reader at 450 nm wavelength.

1.5 NO Inhibitory Assay

RAW 264.7 cells were seeded in 24-well plates at a density of $5 \times 10^5$ cells/ml, and then incubated with or without LPS (1 µg/ml) in the absence or presence of tested samples for 24 h. The effects of the tested samples on NO production were measured indirectly by analysis of nitrite levels using the Griess reaction.

1.6 NF-κB Reporter Assay

RAW-Blue™ cells, RAW 264.7 macrophages which stably express a secreted embryonic alkaline phosphatase (SEAP) gene inducible by NF-κB, were seeded in 60 mm dishes at a density of $5 \times 10^5$ cells/ml, and grown overnight in a 5% $CO_2$ incubator at 37° C. Cells were pretreated with compound 1h for 30 min followed by LPS stimulating for 24 h, and then the medium was harvested. Medium (20 µl) were then mixed with QUANTI-Blue™ (InvivoGen) medium (200 µl) in 96-well plates at 37° C. for 15 min. Results of the SEAP activity were assessed by measuring the optical density at 655 nm using an ELISA reader.

1.7 Western Blot Assay

Whole cell lysates were separated by SDS-PAGE and electrotransferred to a PVDF membrane. The membranes were incubated in blocking solution—5% nonfat milk in phosphate buffered saline with 0.1% Tween 20—at room temperature for 1 h. Each membrane was incubated with a specific primary antibody at room temperature for 2 h. After washing three times in PBS with 0.1% Tween 20, the membrane was incubated with an HRP-conjugated secondary antibody directed against the primary antibody. The membrane was developed by an enhanced chemiluminescence Western blot detection system.

1.8 Measurement of Intracellular ROS Production

Intracellular ROS stimulated by LPS was measured by detecting the fluorescence intensity of the 2',7'-dichlorofluorescein diacetate ($H_2DCFDA$) oxidized product (DCF) (Molecular Probes, Eugene, Oreg.). Briefly, for LPS-induced ROS production, RAW 264.7 macrophages ($5 \times 10^5$/ml) were grown in a phenol red-free RPMI medium for 24 h and then pretreated with $H_2DCFDA$ (2 µM), compound 1h (20 µM), or NAC (10 mM) at 37° C. for 30 min followed by LPS stimulating for the time as indicated. For ATP-induced ROS production, LPS-primed J774A.1 macrophages ($5 \times 10^5$/ml) were grown in a phenol red-free RPMI medium for 6 h and then pretreated with $H_2DCFDA$ (2 µM), compound 1h (20 µM), or NAC (10 mM) at 37° C. for 30 min followed by ATP stimulating for the time as indicated. The relative fluorescence intensity of fluorophore DCF, formed by peroxide oxidation of the non-fluorescent precursor, was detected at an excitation wavelength of 485 nm and an emission wavelength of 530 nm with a microplate absorbance reader (Bio-Rad Laboratories, Inc).

1.9 Measurement of NF-κB p65 Nuclear Translocation

Nuclear protein from RAW 264.7 and J774A.1 cells were extracted using a Nuclear Extract Kit (Active Motif) according to the manufacturer's instructions and nuclear NF-κB p65 activation quantified using an ELISA-based TransAM NF-κB kit (Active Motif, Tokyo, Japan) according to the manufacturer's protocol by reading the absorbance with a microplate absorbance reader (Bio-Rad Laboratories, Inc) at 450 nm with a reference wavelength of 655 nm.

1.10 Statistical Analysis

All values are given as mean±SD. Data analysis involved one-way ANOVA with a subsequent Scheffé test.

2. Results 2.1 Effect of polyenylpyrrole Derivatives on the Viability of Macrophages The aim of this study is to identify non-toxic polyenylpyrrole derivatives which can be used as anti-inflammatory agents. Compounds 1a-n were evaluated for their cytotoxicities against the murine macrophages cell line RAW 264.7 after 24 h treatment. As shown in Table 2, compounds 1a-g exhibited high cytotoxicity against RAW 264.7 cells with $IC_{50}$ below 10 μM, indicating that these compounds are not suitable for further evaluation of their anti-inflammatory activities. The non-cytotoxic compounds 1h-n exhibited anti-inflammatory activity by reducing NO production in LPS-activated macrophages. The three most potent compounds are 1h, 1i and 1n with $ED_{50}$ values of 15±2, 16±2 and 17±2 μM respectively.

TABLE 2

| Sample[a] | $R^1$ | $R^2$ | $R^3$ | Ar | $IC_{50}$ | $ED_{50}$ |
|---|---|---|---|---|---|---|
| 1a | H | H | Me | 3-chloropyrrol-2-yl | <10 μM[b] | N.D. |
| 1b | Me | H | Me | 3-chloropyrrol-2-yl | <10 μM | N.D. |
| 1c | nBu | H | Me | 3-chloropyrrol-2-yl | <10 μM | N.D. |
| 1d | H | Me | Me | 3-chloropyrrol-2-yl | <10 μM | N.D. |
| 1e | Me | Me | Me | 3-chloropyrrol-2-yl | <10 μM | N.D. |
| 1f | Me | Et | Me | 3-chloropyrrol-2-yl | <10 μM | N.D. |
| 1g | nBu | Me | Me | 3-chloropyrrol-2-yl | <10 μM | N.D. |
| 1h | H | H | H | 3-chloropyrrol-2-yl | >100 μM | 15 ± 2 μM |
| 1i | Me | H | H | 3-chloropyrrol-2-yl | >100 μM | 16 ± 2 μM |
| 1j | H | H | Me | 3-chlorothiophen-2-yl | >100 μM | 29 ± 6 μM |
| 1k | Me | H | Me | 3-chlorothiophen-2-yl | >100 μM | 18 ± 2 μM |
| 1l | Me | H | Me | 2-chlorophenyl | >100 μM | 18 ± 3 μM |
| 1m | Me | H | Me | 3-chlorophenyl | >100 μM | 26 ± 3 μM |
| 1n | Me | H | Me | 3-chloro-1-mesyl-pyrrol-2-yl | >100 μM | 17 ± 2 μM |

[a]$IC_{50}$ value expressed as the mean value of triplicate wells from at least three experiments by AlamarBlue ® assay.
[b]The $ED_{50}$ values that elicited a 50% inhibition of the LPS-induced NO generation.
N.D.: non-determined.

Figure 2:
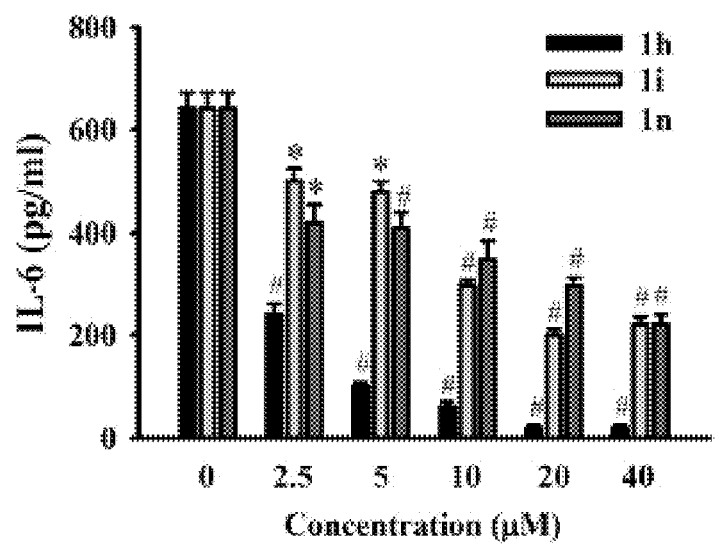
FIG. 2 shows the effect of polyenylpyrrole derivatives on the expression of inflammatory mediators in RAW 264.7 macrophages. In (A) and (C), cells ($5\times10^5$/ml) were incubated with polyenylpyrrole derivatives or DMSO (vehicle) for 30 min followed by stimulating with LPS (1 µg/ml) for 24 h, then NO (A), IL-6 and TNF-α (C) concentration in culture medium were assayed by Griess reaction and ELISA, respectively. In (B), cells ($5\times10^5$/ml) were pretreated with polyenylpyrrole derivatives or DMSO for 30 min followed by stimulating with LPS (1 µg/ml) for 24 h, then the protein expression of iNOS and COX-2 were assayed by Western blot. In (A) and (C), the data are expressed as the mean±SD for three separate experiments, while in (B), the results are representative of those obtained in three different experiments and the histogram shows the quantification expressed as the mean±SD. *, **, and # indicate a significant difference at the level of $p<0.05$, $p<0.01$, $p<0.001$ respectively compared to LPS group.
Figure 2:
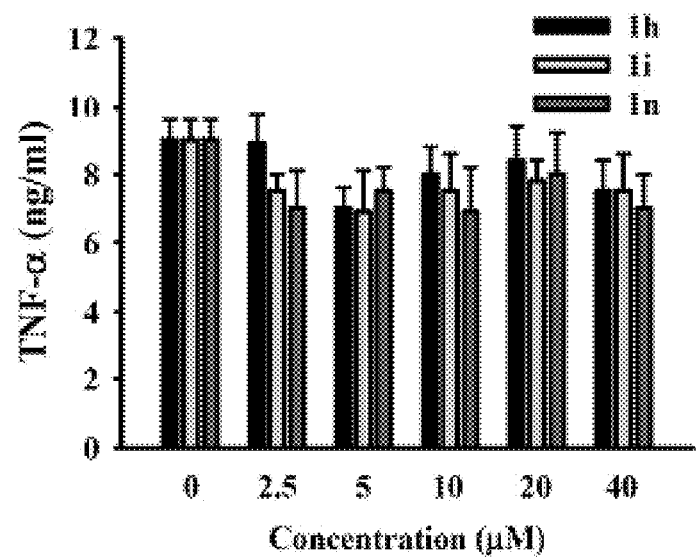

2.2 Compounds 1h, 1i and 1n Decrease Production of NO, iNOS, and IL-6 by LPS-Activated RAW 264.7 Macrophages To investigate the inhibitory effect of compounds 1h, 1i and 1n on the LPS-induced inflammatory responses, the NO levels in the supernatant of LPS-activated RAW 264.7 macrophages cultured with DMSO (vehicle) or compounds 1h, 1i and 1n were measured by Griess reaction. The experimental results indicated that treatment with compounds 1h, 1i and 1n alone did not alter the background level of NO (data not shown), but decreased the production of NO by LPS-activated cells in a dose-dependent manner (FIG. 2A). We next investigated the effect of compounds 1h, 1i and 1n on the protein expression of iNOS, the NO producing enzyme. Treatment with compounds 1h, 1i and 1n reduced the expression of iNOS protein when compared with vehicle in LPS-activated RAW 264.7 macrophages, but did not affect the COX-2 expression, an enzyme producing prostaglandin E2 (FIG. 2B). In addition, we tested the effect of compounds 1h, 1i and 1n on cytokine production by LPS-activated RAW 264.7 macrophages. We found that treatment with compounds 1h, 1i and 1n alone did not alter the background level of IL-6 and TNF-α in macrophages (data not shown), but decreased the secretion of IL-6 by LPS-activated RAW 264.7 macrophages in a dose-dependent manner and compound 1h is more potent than 1i and 1n (FIG. 2C). The TNF-α secretion was slight reduced by compounds 1h, 1i and 1n, but not significantly (FIG. 2C).

Figure 3:
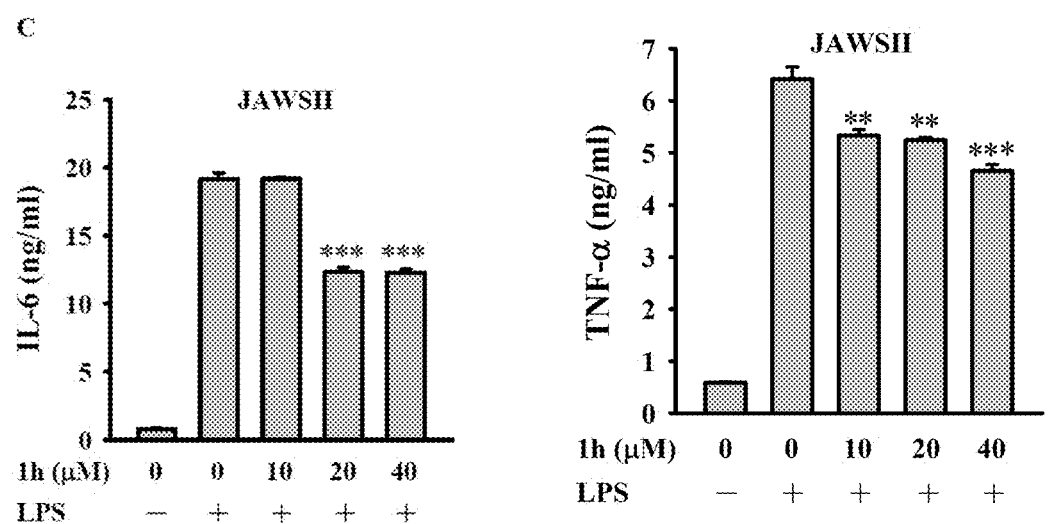
FIG. 3 shows the effect of compound 1h on the secretion of IL-6 and TNF-α in J774A.1 macrophages, peritoneal macrophages, and JAWSII dendritic cells. (A) J774A.1 macrophages ($4\times10^5$/ml), (B) peritoneal macrophages ($4\times10^5$/ml), and (C) JAWSII dendritic cells ($4\times10^5$/ml) were incubated with compound 1h or DMSO for 30 min followed by stimulating with LPS (1 µg/ml) for 24 h, then IL-6 and TNF-α concentration in culture medium were assayed by ELISA. The data are expressed as the mean±SD for three separate experiments. *, , and * indicate a significant difference at the level of $p<0.05$, $p<0.01$, $p<0.001$ respectively compared to LPS group.

2.3 Compound 1h Decreases Secretions of IL-6 and TNF-α by LPS-Activated J774A.1 Macrophages, Peritoneal Macrophages, and JAWSII Dendritic Cells To confirm the anti-inflammatory activity of compound 1h, the effect of compound 1h on LPS-induced cytokine secretion was investigated using another murine macrophages cell line J774A.1 and primary peritoneal macrophages from C57BL/6 mice. We found that compound 1h reduced secretions of IL-6 and TNF-α in both J774A.1 cells (FIG. 3A) and peritoneal macrophages (FIG. 3B). Furthermore, compound 1h also reduced secretions of IL-6 and TNF-α in murine dendritic cell line JAWSII cells (FIG. 3C).

2.4 Compound 1h Reduces IL-1β Secretion Through Inhibiting NLRP3 Inflammasome

Figure 4:
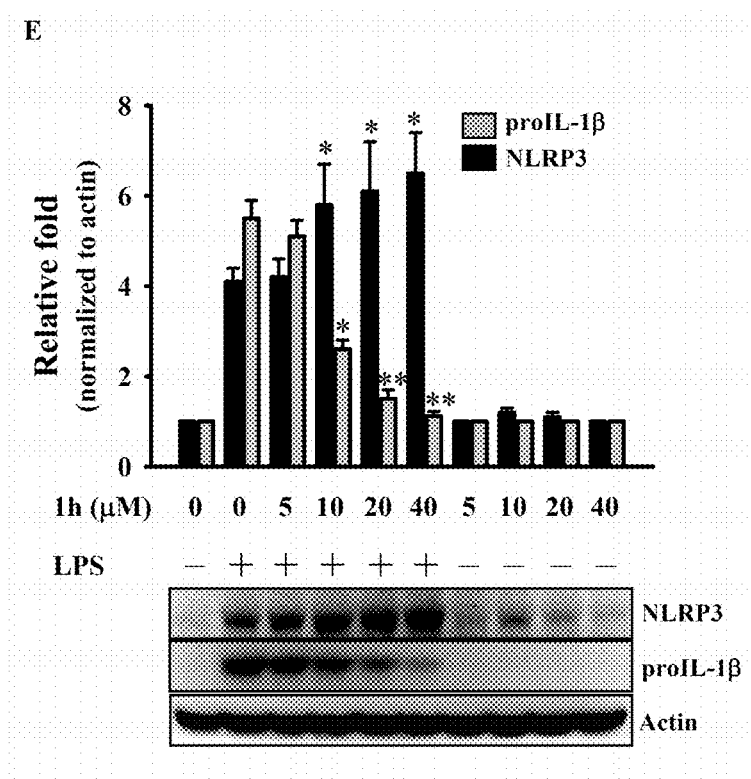
FIG. 4 shows the effect of compound 1h on NLRP3 inflammasome activation in LPS+ATP-activated J774A.1 macrophages. (A) J774A.1 macrophages ($1\times10^6$/ml) and (B) peritoneal macrophages ($1\times10^5$/ml) were incubated with compound 1h for 30 min followed by LPS (1 µg/ml) stimulating for 5.5 h, then the cells were stimulated with ATP (5 mM) for an additional 30 min. The IL-1β in the culture medium was measured by ELISA and the expression of active caspase-1 (p10) was measured by Western blot. In (C) and (D), J774A.1 macrophages ($1\times10^6$/ml) were incubated with LPS (1 µg/ml) for 5.5 h, then cells were incubated with compound 1h for 30 min followed by stimulating with ATP (5 mM) for an additional 30 min. The IL-1β and IL-6 in the culture medium were measured by ELISA and the expression of active caspase-1 (p10) was measured by Western blot. In (E), J774A.1 macrophages ($1\times10^6$/ml) were incubated with compound 1h for 30 min followed by LPS (1 µg/ml) stimulating for 6 h. The expression of NLRP3 and proIL-1β were measured by Western blot. In ELISA, the data are expressed as the mean±SD for three separate experiments, while in Western blot, the results are representative of those obtained in three different experiments and the histogram shows the quantification expressed as the mean±SD. *, , and * indicate a significant difference at the level of p<0.05, p<0.01, and p<0.001 respectively compared to LPS+ATP or LPS group.

ATP is known to activate NLRP3 inflammasome in LPS-primed macrophages which leads to caspase-1 activation and IL-1β secretion (Hu Y et al. (2010) *J Immunol* 185(12): 7699-7705). To test whether compound 1h is able to modulate NLRP3 inflammasome activation, a mouse macrophage cell line, J774A.1, was selected (RAW 264.7 macrophages are not suitable for studying NLRP3 inflammasome). The full activation of the NLRP3 inflammasome requires both a priming signal and an activation signal, and therefore in the present study we investigate whether compound 1h was able to modulate the priming signal and the activation signal of NLRP3 inflammasome. Incubation of cells with compound 1h before LPS and ATP treatment significantly inhibited IL-1β secretion and caspase-1 activation in a dose-dependent manner (FIG. 4A). In the same condition, The IL-1β inhibition activity of compound 1h was confirmed in primary peritoneal macrophages (FIG. 4B). In addition, to examine whether compound 1h was able to affect the ATP-mediated activation signal, we incubated LPS-primed macrophages with compound 1h for 30 min before ATP stimulation and found that the compound 1h inhibited IL-1β secretion, but not caspase-1 activation (FIG. 4C), while compound 1h had no significant effect on IL-6 secretion (FIG. 4D). These results indicated that compound 1h specifically inhibited NLRP3 inflammasome-mediated IL-1β secretion, but not inhibited IL-6 secretion, which is independent of NLRP3 inflammasome. Furthermore, we have tested compound 1h on its ability to inhibit NLRP3 expression (essential component of NLRP3 inflammasome) and proIL-1β (IL-1β precursor) in LPS-activated cells. In this experiment, cells were incubated with compound 1h for 30 min followed by LPS stimulation for another 6 h. We found that compound 1h inhibited LPS-induced proIL-1β expression in a dose-dependent fashion, but increased NLRP3 expression (FIG. 4E).

Figure 5:
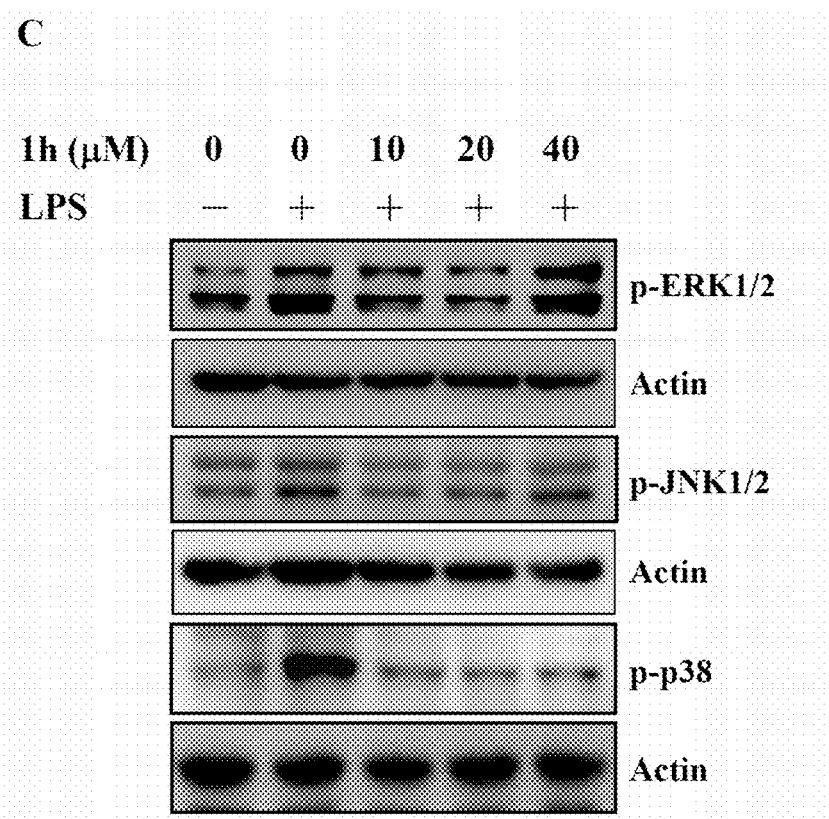
FIG. 5 shows the effect of compound 1h on ROS production and MAPK phosphorylation in LPS-activated macrophages. In (A), RAW 264.7 macrophages ($5\times10^5$/ml) were incubated with compound 1h (20 μM), N-acetyl cysteine (NAC; 10 mM) or DMSO (vehicle) for 30 min followed by LPS (1 μg/ml) stimulating for the indicated time, then ROS levels were measured by detection of the fluorescence intensity of the fluorophore carboxyl-DCF and expressed relative to those at time zero. In (B), RAW 264.7 macrophages ($5\times10^5$/ml) were incubated with compound 1h (20 μM) or DMSO for 30 min followed by LPS (1 μg/ml) stimulating for 0-60 min, then the phosphorylation levels of ERK1/2, JNK1/2, p38 were analyzed by Western blot. In (C), J774A.1 macrophages ($5\times10^5$/ml) were incubated with compound 1h or DMSO for 30 min followed by LPS (1 μg/ml) stimulating for 20 min, then the phosphorylation levels of ERK1/2, JNK1/2, p38 were analyzed by Western blot. In (A), the data are expressed as the mean±SD for three separate experiments, while in (B) and (C), the results are representative of those obtained in three different experiments and the histogram shows the quantification expressed as the mean±SD. * indicates a significant difference at the level of p<0.05 compared to LPS group.

2.5 Compound 1h Inhibits ROS Production and MAPK Activation in LPS-Activated Macrophages ROS have been demonstrated to play important roles in LPS-mediated cytokine expression (Hsu H Y, Wen M H. supra; Liao P C et al., supra). To test whether compound 1h mediated anti-inflammatory effect in LPS-activated cells through down-regulation of ROS production, the intracellular ROS production in LPS-activated RAW 264.7 macrophages was measured. We found that LPS stimulation of cells rapidly induced ROS production and pretreatment with N-acetyl cysteine (NAC), a potent antioxidant, reduced ROS production. Compound 1h was able to reduce LPS-stimulated ROS production, suggesting that the anti-inflammatory effect of compound 1h could have been mediated partially through its antioxidative activity (FIG. 5A).

LPS potently induces macrophage activation and the production of pro-inflammatory cytokines by the activation of TLR4 through many signaling pathways, including the MAPK signaling pathways (Su S C et al. (2006) *Clin Chim Acta* 374(1-2): 106-115). To examine whether the effects of compound 1h on LPS-induced macrophages are associated with MAPK signaling cascades, RAW 264.7 macrophages were treated with LPS in the presence or absence of compound 1h. The phosphorylation levels of MAPK, including ERK1/2, JNK1/2 and p38 were determined by Western blot analysis. The experimental results showed that compound 1h inhibited the phosphorylation levels of ERK1/2, JNK1/2, and p38 in LPS-activated RAW 264.7 macrophages (FIG. 5B). These results were confirmed in J774A.1 macrophages (FIG. 5C). These results indicate that compound 1h inhibits the activation of the MAPK signaling cascades in LPS-activated macrophages.

2.6 Compound 1h Inhibits NF-κB Activation in LPS-Activated Macrophages

Figure 6:
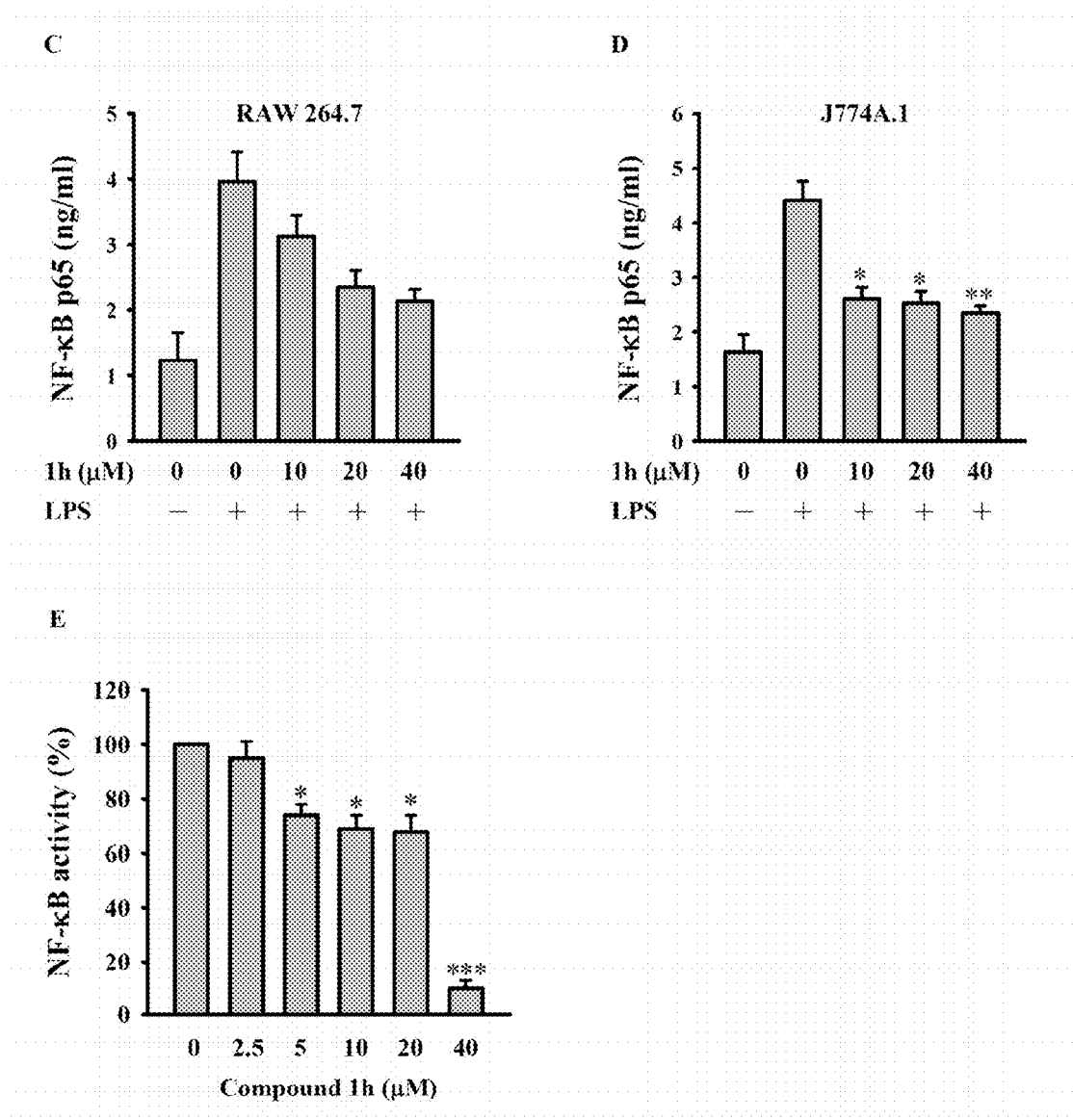
FIG. 6 shows of compound 1h on NF-κB activation in LPS-activated macrophages. (A) RAW 264.7 macrophages ($5\times10^5$/ml) or (B) J774A.1 macrophages ($5\times10^5$/ml) were incubated with compound 1h or DMSO for 30 min followed by LPS (1 μg/ml) stimulating for 20 min, then the phosphorylation levels of IKK-α and IκB-α and total IκB-α protein level were analyzed by Western blot. (C) RAW 264.7 macrophages ($5\times10^5$/ml) or (D) J774A.1 macrophages ($5\times10^5$/ml) were incubated with compound 1h (10-40 μM) or DMSO for 30 min followed by LPS (1 μg/ml) stimulating for 20 min, then the nuclear translocation of NF-κB were analyzed by ELISA. (E) RAW-Blue™ cells ($5\times10^5$/ml) were incubated with compound 1h (2.5-40 μM) or DMSO for 30 min followed by LPS (1 μg/ml) stimulating for 24 h, then the SEAP activity was measured by QUANTI-Blue™. In (A) and (B), the results are representative of those obtained in three different experiments and the histogram shows the quantification expressed as the mean±SD. p-IKK-α and p-IκB-α are normalized to IKK-α and actin respectively. In (C), (D), and (E), the data are expressed as the mean±SD for three separate experiments. *, , and * indicate a significant difference at the level of p<0.05, p<0.01, and p<0.001 respectively compared to LPS group.

In resting macrophages, NF-κB is sequestered in the cytoplasm as an inactive precursor complex by its inhibitory protein, IκB. Upon LPS stimulation, IκB is phosphorylated by IκB kinase (IKK), ubiquitinated, and rapidly degraded via proteasomes to release NF-κB (Baeuerle P A. (1998) *Cell* 95: 729-731). In determining whether compound 1h could inhibit LPS-stimulated NF-κB signaling in macrophages, we found that compound 1h inhibited the phosphorylation levels of IKK-α and IκB-α, and partially rescued IκB-α degradation in LPS-activated RAW 264.7 macrophages (FIG. 6A) and J774A.1 macrophages (FIG. 6B). In addition, compound 1h inhibited NF-κB nuclear translocation in both RAW 264.7 (FIG. 6C) and J774A.1 macrophages (FIG. 6D). Furthermore, by using NF-κB-dependent alkaline phosphatase reporter cells, we demonstrated that NF-κB transcriptional activity in LPS-stimulated macrophages was also reduced by compound 1h (FIG. 6E). These results indicate that compound 1h inhibits the activation of the NF-κB signaling cascades in LPS-activated macrophages.

Figure 7:
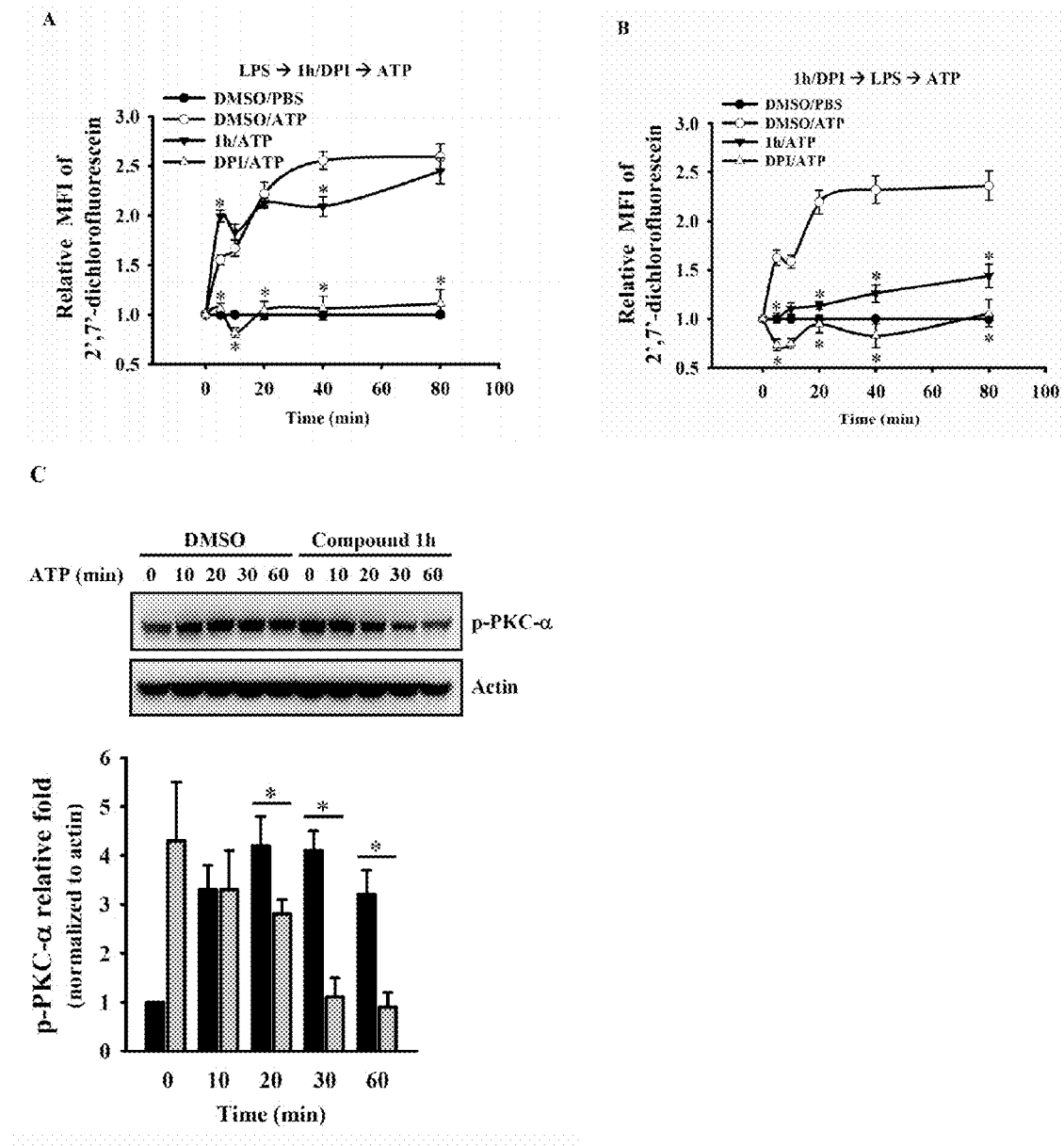
FIG. 7 shows the effect of compound 1h on ROS production and PKC-α phosphorylation in ATP-activated macrophages. In (A), J774A.1 macrophages ($1\times10^6$/ml) were incubated with LPS (1 μg/ml) for 5.5 h and then incubated with compound 1 h (20 M), DPI (100 μM), or DMSO (vehicle) for 30 min followed by ATP (5 mM) stimulating for the indicated time, then ROS levels were measured by detection of the fluorescence intensity of the fluorophore carboxyl-DCF and expressed relative to those at time zero. In (B), J774A.1 macrophages ($1\times10^6$/ml) were incubated with compound 1h (20 μM), DPI (100 μM), or DMSO (vehicle) for 30 min followed by LPS (1 μg/ml) stimulating for 5.5 h, then the cells were stimulated with ATP (5 mM) for the indicated time. The ROS levels were measured by detection of the fluorescence intensity of the fluorophore carboxyl-DCF and expressed relative to those at time zero. In (C), LPS-primed J774A.1 macrophages ($1\times10^6$/ml) were incubated with compound 1h (20 μM) or DMSO (vehicle) for 30 min followed by ATP (5 mM) stimulating for 0-60 min, then the phosphorylation level of PKC-α was analyzed by Western blot. In (A) and (B), the data are expressed as the mean±SD for three separate experiments, while in (C), the results are representative of those obtained in three different experiments and the histogram shows the quantification expressed as the mean±SD. * indicates a significant difference at the level of p<0.05 compared to ATP group.

2.7 Compound 1h Inhibits ROS Production and PKC-α Phosphorylation in ATP-Activated Macrophages ATP induces ROS production through NADPH oxidase is required for caspase-1 activation and IL-1β secretion in macrophages (Moore S F, MacKenzie A B. (2009) *J Immunol* 183(5): 3302-3308; Cruz C M et al. (2007) *J Biol Chem* 282(5): 2871-2879). To determine whether compound 1h-mediated IL-1β down-regulation occurs via the inhibition of ATP-induced ROS production, LPS-primed cells were first incubated with compound 1h for 30 min before ATP stimulation. We found that compound 1h reduces ATP-induced ROS production slightly (FIG. 7A) but inhibited ATP-induced ROS production significantly when it added before LPS priming (FIG. 7B). In addition, we also found that compound 1h inhibited ATP-induced PKC-α phosphorylation in LPS-primed cells (FIG. 7C).

In summary, we have identified compounds 1h-1n which were able to inhibit LPS-induced NO production without reducing cell viability. Among them, we further demonstrated compounds 1h, 1i and 1n decreased production of NO, iNOS and IL-6 in LPS activated macrophages, and compound 1h inhibited NLRP3 inflammasome activation as well as NO and IL-6 expression through the reduction of both LPS- and ATP-induced ROS production and LPS-induced activation of MAPK and NF-κB. The compounds of the invention, particularly compound 1h, could be applicable for use in the development of anti-inflammatory therapeutic.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

We claim:

1. A method for treating inflammation comprising administering a subject in need thereof with a therapeutically effective amount of a compound of formula (I):

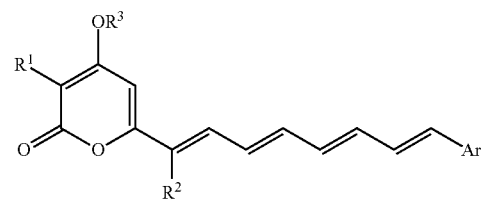

wherein $R^1$, $R^2$ and $R^3$ independently are H or an alkyl, and Ar is an aryl group or a five-membered heteroaryl group containing one, two or three heteroatoms selected from the group consisting of N, O and S, wherein the aryl group and the heteroaryl group are unsubstituted or substituted by one or two substituents independently selected from the group consisting of halo and mesyl, provided that when $R^3$ is a methyl group, Ar is not a 3-chloropyrrolyl group, or a pharmaceutically acceptable salt thereof, wherein the compound of formula (I) is in a therapeutically effective amount to (i) inhibit production of nitric oxide (NO) or expression of inducible nitric oxide synthase (iNOS), interleukin-6 (IL-6) or tumor necrosis factor-α (TNF-α), (ii) inhibit NLRP3 inflammasome-mediated IL-1β expression, or (iii) inhibit reactive oxygen species (ROS) production, mitogen-activated protein kinase (MAPR) phosphorylation, NF-κB activation or protein kinase C (PKC) activation, in macrophages or dendritic cells of the subject.

2. The method of claim 1, wherein the aryl group is a 6-membered monocyclic, 10-membered bicyclic, or 14-membered tricyclic aryl group, being unsubstituted or substituted by one or two substituents independently selected from the group consisting of halo and mesyl.

3. The method of claim 2, wherein the aryl group is selected from the group consisting of phenyl, naphthyl, pyrenyl, anthryl, and phenanthryl, being unsubstituted or substituted by one or two substituents independently selected from the group consisting of halo and mesyl.

4. The method of claim 1, wherein the five-membered heteroaryl group is selected from the group consisting of pyrrolyl, furanyl, thiophenyl, oxazolyl, isoxazolyl, pyrazolyl, thiazolyl, isothiazolyl, triazolyl, oxadiazolyl, and thiadiazolyl, being unsubstituted or substituted by one or two substituents independently selected from the group consisting of halo and mesyl.

5. The method of claim 1, wherein $R^1$ and $R^3$ are independently H or methyl, and $R^2$ is H.

6. The method of claim 1, wherein Ar is selected from the group consisting of 3-chloropyrrol-2-yl, 3-chlorothiophen-2-yl, 2-chlorophenyl, and 3-chloro-1-mesyl-pyrrol-2-yl.

7. The method of claim 1, wherein the compound of formula (I) is selected from the group consisting of compound 1h, compound 1i, compound 1j, compound 1k, compound 1l, compound 1m and 1n, having the structures as follows:

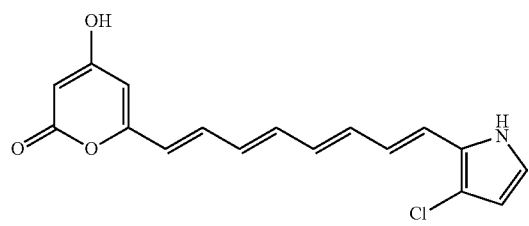

1h

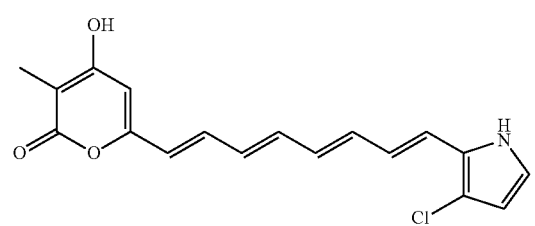

1i

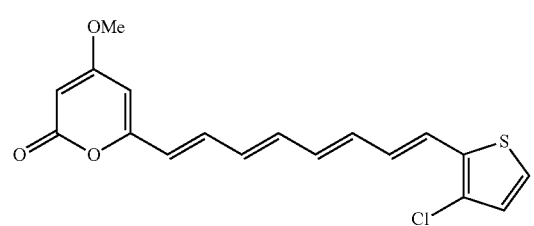

1j

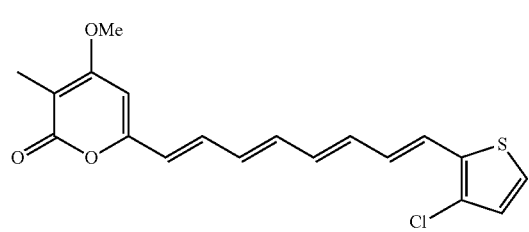

1k

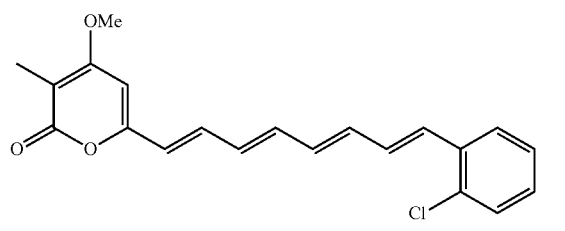

1m

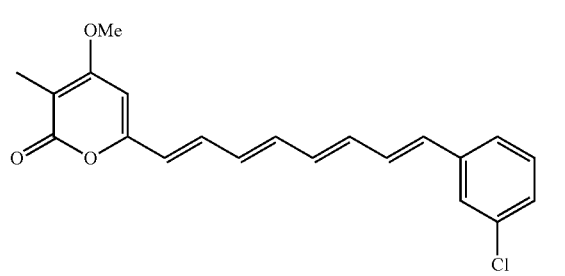

1n

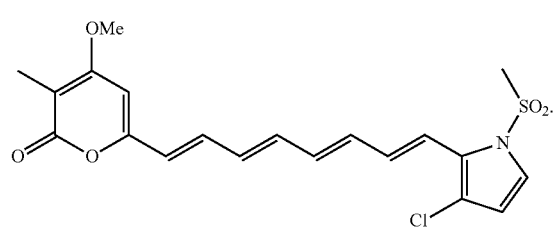

8. The method of claim 1, wherein the compound of formula (I) is compound 1h, 1i or 1n, having the structures as follows:

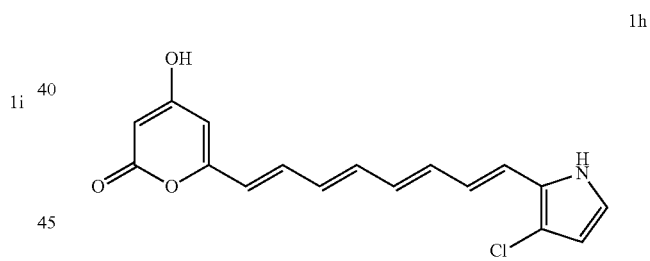

1h

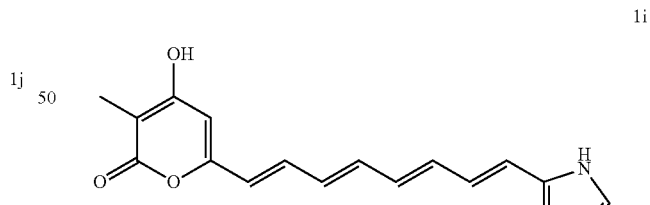

1i

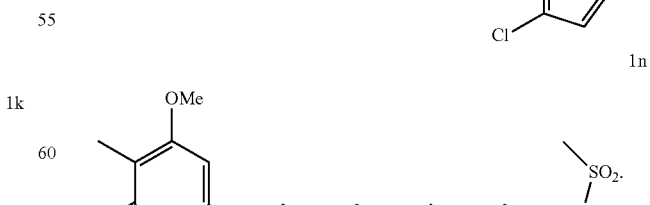

1n

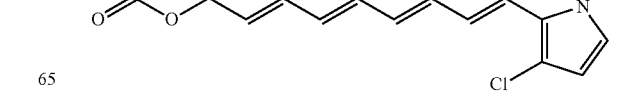

9. A method for reducing inflammatory responses comprising administering a subject in need thereof with a therapeutically effective amount of a compound of formula (I):

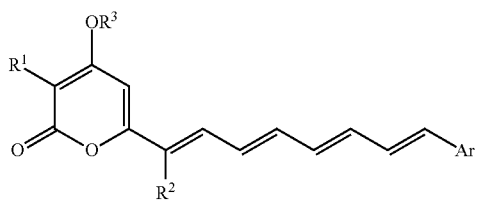

wherein $R^1$, $R^2$ and $R^3$ independently are H or an alkyl, and Ar is an aryl group or a five-membered heteroaryl group containing one, two or three heteroatoms selected from the group consisting of N, O and S, wherein the aryl group and the heteroaryl group are unsubstituted or substituted by one or two substituents independently selected from the group consisting of halo and mesyl, provided that when $R^3$ is a methyl group, Ar is not a 3-chloropyrrolyl group, or a pharmaceutically acceptable salt thereof wherein the compound of formula (I) is in a therapeutically effective amount to (i) inhibit production of nitric oxide (NO) or expression of inducible nitric oxide synthase (iNOS), interleukin-6 (IL-6) or tumor necrosis factor-α (TNF-α), (ii) inhibit NLRP3 inflammasome-mediated IL-1β expression, or (iii) inhibit reactive oxygen species (ROS) production, mitogen-activated protein kinase (MAPR) phosphorylation, NF-κB activation or protein kinase C (PKC) activation, in macrophages or dendritic cells of the subject.

10. The method of claim 9, wherein the aryl group is a 6-membered monocyclic, 10-membered bicyclic, or 14-membered tricyclic aryl group, being unsubstituted or substituted by one or two substituents independently selected from the group consisting of halo and mesyl.

11. The method of claim 10, wherein the aryl group is selected from the group consisting of phenyl, naphthyl, pyrenyl, anthryl, and phenanthryl, being unsubstituted or substituted by one or two substituents independently selected from the group consisting of halo and mesyl.

12. The method of claim 9, wherein the five-membered heteroaryl group is selected from the group consisting of pyrrolyl, furanyl, thiophenyl, oxazolyl, isoxazolyl, pyrazolyl, thiazolyl, isothiazolyl, triazolyl, oxadiazolyl, and thiadiazolyl, being unsubstituted or substituted by one or two substituents independently selected from the group consisting of halo and mesyl.

13. The method of claim 9, wherein $R^1$ and $R^3$ are independently H or methyl, and $R^2$ is H.

14. The method of claim 9, wherein Ar is selected from the group consisting of 3-chloropyrrol-2-yl, 3-chlorothiophen-2-yl, 2-chlorophenyl, and 3-chloro-1-mesyl-pyrrol-2-yl.

15. The method of claim 9, wherein the compound of formula (I) is selected from the group consisting of compound 1h, compound 1i, compound 1j, compound 1k, compound 1l, compound 1m and 1n, having the structures as follows:

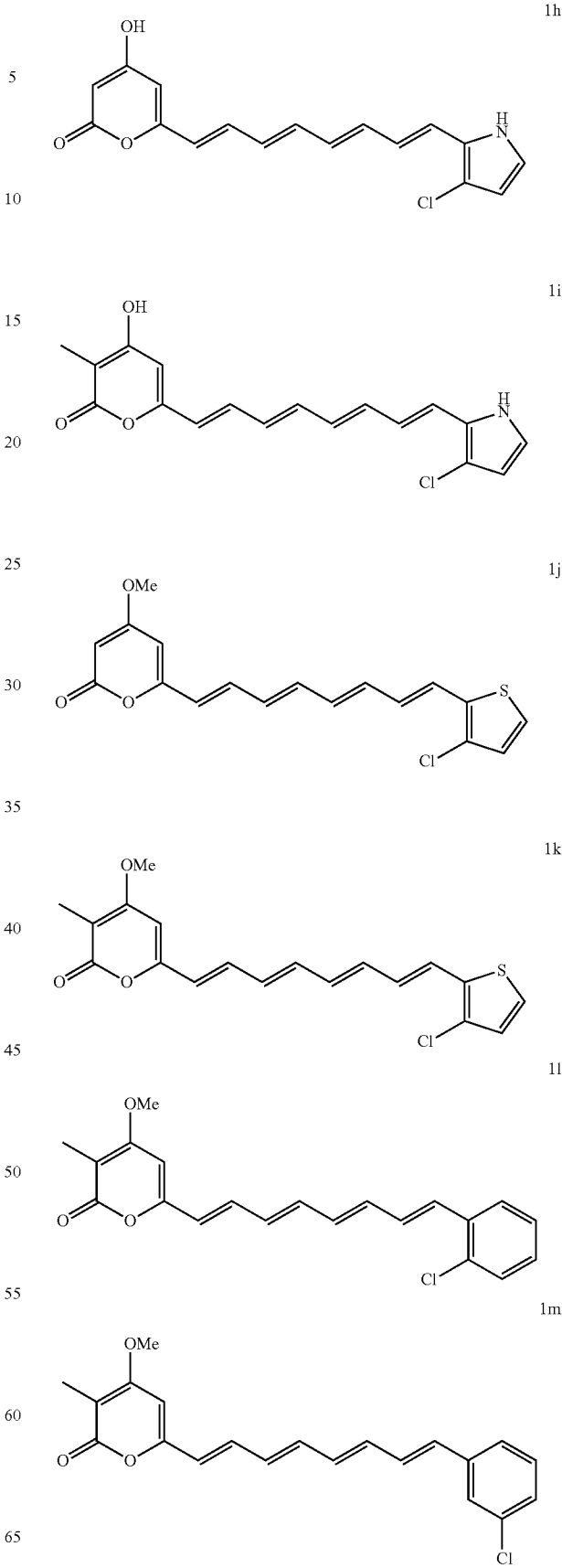

-continued
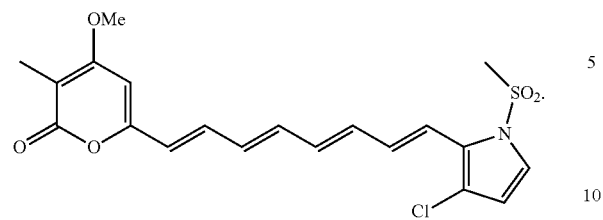
1n
16. The method of claim 9, wherein the compound of formula (I) is compound 1h, 1i or 1n, having the structures as follows:
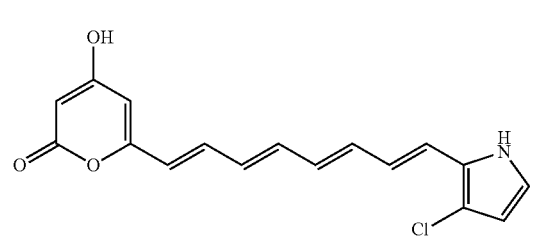
1h
-continued
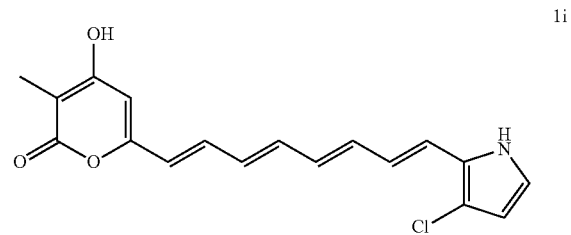
1i
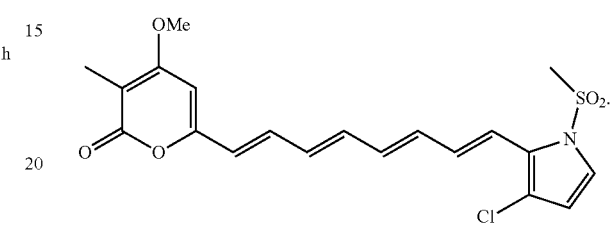
1n
* * * * *